United States Patent
Petersson

(10) Patent No.: US 7,208,170 B2
(45) Date of Patent: Apr. 24, 2007

(54) POWDER TEAT DIP GERMICIDE, FUNGICIDE AND SKIN CONDITIONER

(76) Inventor: Lennart G. Petersson, 229 SE. Main St., Douglas, MA (US) 01516

( * ) Notice: Subject to any disclaimer, the term of this patent is extended or adjusted under 35 U.S.C. 154(b) by 325 days.

(21) Appl. No.: 10/660,880

(22) Filed: Sep. 10, 2003

(65) Prior Publication Data
US 2004/0058011 A1 Mar. 25, 2004

Related U.S. Application Data

(60) Provisional application No. 60/412,259, filed on Sep. 20, 2002.

(51) Int. Cl.
*A01N 25/32* (2006.01)
(52) U.S. Cl. .................. 424/406; 424/405; 424/409; 424/421; 424/438; 424/641; 424/642; 514/635
(58) Field of Classification Search ............... 424/406, 424/438, 641, 642; 514/635
See application file for complete search history.

(56) References Cited

U.S. PATENT DOCUMENTS 5,399,353 A * 3/1995 Bartnik et al. .............. 424/438
6,037,386 A * 3/2000 Modak et al. .............. 523/105

* cited by examiner

*Primary Examiner*—Neil S. Levy
(74) *Attorney, Agent, or Firm*—Terry M. Crellin

(57) ABSTRACT

A non-toxic, germicide, fungicide and healing composition and a method of topically applying the composition in powdered form to the skin of domesticated farm animals including dairy cattle are disclosed. The composition comprises (a) finely divided, particulate chlorhexidine-containing material, (b) finely divided, particulate zinc-containing material and (c) an inert powdered carrier, with the chlorhexidine-containing material and the zinc-containing material being present in an amount to achieve effective germicidal activity. The chlorhexidine-containing material is preferably chlorhexidine acetate. The zinc-containing material is preferably selected from the group consisting of zinc stearate, zinc chloride, zinc nitrate, zinc oleate, zinc oxide, zinc phosphate, zinc peroxide, zinc iodide, elemental zinc and mixtures thereof.

6 Claims, No Drawings

POWDER TEAT DIP GERMICIDE, FUNGICIDE AND SKIN CONDITIONER

CROSS REFERENCE TO RELATED APPLICATION

This application claims the filing date of Provisional Application No. 60/412,259 filed on Sep. 20, 2002.

BACKGROUND OF THE INVENTION

1. Field of the Invention

The invention relates to a non-toxic, germicide, fungicide and healing compositions, and in particular to such compositions which are adapted to be applied topically to dairy cattle and other domesticated farm animals.

2. State of the Art

Chlorhexidine has been used as a germicidal and fungicidal agent for application to farm animals and as an aid in reducing bacterial populations on the skin. Chlorhexidine has also been used in teat dip sanitizers for similar purposes. All such previous teat dip sanitizers of the prior art are of liquid form and the chlorhexidine is used in the form of a gluconate. There is no suggestion in the prior art of a powdered composition that contains chorhexidine and which is to be used as a germicidal agent to be applied to the skin of farm animals. There is further no suggestion in the prior art of using chlorhexidine acetate as a germicidal agent in a powdered composition for application to the skin of farm animals.

Unfortunately, under some environmental conditions, the use of a germicidal agent in the form of a liquid composition which is applied to the skin of farm animals is not conducive to maintaining good skin conditions of the animals. Especially, under conditions of severe cold and wind, skin condition can be severely challenged by the use of a liquid teat dip sanitizer inasmuch as the skin can freeze due to the liquid that is applied on the skin. It would be highly desirable to provide a non-liquid composition, and in particular a powdered composition, so as to prevent the freezing and damage to the skin of the animal which otherwise results from such freezing. It is also desirable to provide a germicidal agent in the form of a powder for general use in veterinary medicine, particularly as a topical dressing for treatment of infections, burns, sores, cuts and abrasions in dairy cattle and other domestic farm animals. It would be further advantageous to provide such a powdered germicidal agent that further has the capability of providing rapid healing of the damaged tissue.

OBJECTIVES AND BRIEF DESCRIPTION OF THE INVENTION

A principal objective of the invention is to provide a novel germicidal and fungicidal agent in the form of a powdered composition which is to be applied to the skin of domesticated farm animals such as dairy cattle.

A further objective of the present invention is to provide such a powdered germicidal and fungicidal agent that can be applied to the skin of the farm animal especially during exposure to severe cold and windy conditions.

A still further objective of the present invention is to provide such a powdered germicidal and fungicidal agent which can be applied to the teats of lactating dairy cattle as an effective germicide and fungicide for preventing intra mammary infections, especially under conditions where the environment is not conducive to maintaining good skin and teat end conditions, such as under conditions of severe cold and wind.

The above objectives are achieved in accordance with the present invention by providing a novel, non-toxic, germicide, fungicide and healing agent in the form of a powdered composition containing chlorhexidine, a finely divided, particulate zinc-containing material and an inert powdered carrier. The carrier can be any solid material such as cornstarch which, when applied in powdered form, is inert to the skin and teats of dairy animals and other domesticated farm animals.

The chlorhexidine is present in the form of finely divided, particulate chlorhexidine acetate. Zinc is present in the form of a finely divided, particulate, zinc-containing material selected from the group consisting of zinc stearate, zinc chloride, zinc nitrate, zinc oleate, zinc oxide, zinc phosphate, zinc peroxide, zinc iodide, elemental zinc and mixtures thereof. The chlorhexidine acetate and zinc-containing material are present in an amount to achieve effective germicidal activity. Generally, the chlorhexidine acetate is present in an amount of from about 0.1% to about 12% by weight. Preferably, the concentration of chlorhexidine acetate is between about 0.2% and about 5% by weight. The zinc-containing material is generally present in an amount of from about 0.1% to about 15% by weight. Preferably, the concentration of zinc-containing material is between about 0.5% and about 6% by weight.

The present invention provides a dry composition in which the carrier is effective in holding the active ingredients on the skin surface. The composition is particularly adapted to be used during cold and wet winter months on the teats of dairy cows. The present invention, with its dry composition is obviously effectively used during all seasons with positive results. A teat dip formulated for being applied wet to the teats and skin of animals during wet, cold and windy conditions can cause chapping and damage caused by freezing of the skin tissue. In contrast, the present invention applied dry to skin will not have similar detrimental effects. In addition, it will have a positive effect by a significant reduction of the bacterial flora on the skin. It is also well accepted that there is a positive correlation between skin and teat end condition to the level of new clinical cases of mastitis. Therefore, in help to maintain good skin condition and the reduction of the bacterial load on the teat skin, the present invention should aid in the prevention on new clinical and sub-clinical cases of mastitis in lactating dairy cows.

Additional objects and features of the invention will become apparent from the following detailed description.

DETAILED DESCRIPTION OF THE PREFERRED EMBODIMENTS

In accordance with the present invention, a non-toxic, germicide, fungicide and healing composition is made by mixing together particulate, finely divided chlorhexidine acetate, particulate, finely divided, zinc-containing material as defined above and an inert, powdered carrier. The carrier can be any powdered, solid material which, when applied in powdered form, is inert to the skin and teats of dairy animals and other domesticated farm animals. Preferably, the carrier is cornstarch. The composition is easily and readily prepared by simple mixing of the ingredients. It has been demonstrated that the novel composition of the present invention in its dry, powdered form when applied to the skin of dairy cattle and other domesticated farm animals will kill bacteria of many types such as *Staphylococcus aureus* and *Streptococcus agalactiae* and environmental pathogens. In addition, the novel germicide composition of the present invention is also an effective fungicide and will also aid in the healing of damaged skin caused by environmental conditions, as well as cuts, cracks and other abnormal modifications of the tissue. It has further been found that when the novel germicide and fungicide composition of the present invention is applied to the skin of dairy cattle who have open sores and/or well developed skin infections, with the composition being applied between the mammary gland (udder) and the rear legs or other areas, the open sores and severe skin infections can be cured after a couple of applications. There are good indications that the novel germicide and fungicide composition of the present invention is also effective against a variety of other skin ailments in animals.

The novel germicide and fungicide composition of the present invention was tested for it's efficacy under experimental conditions using bacterial challenges with *Staphyococcus aureus* and *Streptococcus agalactiae* organisms. The titer of the two organisms was applied to the teats of lactating dairy cows. The teats of the animals in the control group, which was comprised of half of the animals, were dipped in the titer of the organisms. The teats were then rinsed with a growth media quencher, and the resulting solution was collected in a vial and subsequently plated on a petri dish with growth media. The test group that the composition of the present invention was tested on first had their teats dipped in the titer of the organisms, and the powdered teat dip composition of the present invention was then applied to the teats. The powdered teat dip was allowed to stay on the teats for three minutes. The subsequent rinse and collection was then performed according to the protocol mentioned above. These procedures were repeated for ten consecutive days. The Geometric Mean Total Bacteria Counts recovered from the rinse solution of the teats were as follows:

|  | Control Group | Test Group |
|---|---|---|
| Total Bacterial Counts | 272547.1 | 31.48 |
| *Streptococcus agalactiae* | 273.23 | 11.46 |
| *Staphylococcus aureus* | 327.57 | 13.24 |

This study was conducted at the University of Washington School of Veterinary Medicine.

The novel composition of the present invention was further tested in Vermont and Massachusetts during the winter of 2001, and these tests related directly to skin conditioning and acceptability of the novel composition relative to use and appearance of the composition. The use of the composition was initiated on one farm in Vermont where skin condition was a problem. After the results obtained during a short trial (one week) with a couple of cows with severe skin condition, the entire herd was then dipped with the novel composition. The initial short trial made such an improvement on the initial animals that the farm chose to apply the novel composition to all the cows in the herd.

In another test of cows that had lesions that were suspected to be caused by virus related conditions and which were especially persistent through the winter months, a control group of 10 cows were treated by dipping their teats before milking with a 0.5% iodophore liquid teat dip containing 10% glycerin as a skin conditioning agent. Half of the cows in the control group had their teats dipped after milking with the same iodophore teat dip. The other 5 cows had their teats treated with the novel, powdered teat dip composition of the present invention after being milked. After 10 days of following the procedure given above, the 5 cows using the novel, powdered teat dip of the present invention all showed significant reduction in the lesions on the teats. On one cow the lesions could be pulled off the teats with perfectly new, good skin underneath. Of the 5 cows using the iodophore teat dip, one showed a very slight improvement and the other 4 showed no change in the lesions.

A dairy farm in Vermont had an epidemic of dermatophytosis (ringworm), which is caused by an infection by primarily three genera of fungi called dermatophytes. The germicide and fungicide composition of the present invention was used and a significant reduction of the infection was achieved.

The invention claimed is:

1. A method of treating skin of dairy cattle, said method comprising applying a non-toxic, germicide, fungicide and healing composition in powdered form topically to said skin, said composition comprising (a) finely divided, particulate chlorhexidine acetate, (b) finely divided, particulate zinc-containing material selected from the group consisting of zinc chloride, zinc nitrate, zinc oxide, zinc phosphate, zinc peroxide, zinc iodide, elemental zinc and mixtures thereof and (c) an inert, powdered carrier, with said chlorhexidine acetate and said zinc-containing material being present in an amount to achieve effective germicidal activity.

2. The method in accordance with claim 1 wherein said zinc-containing material is present in an amount of from about 0.1% to about 15% by weight, and wherein said chlorhexidine acetate is present in an amount of from about 0.1% to about 12% by weight.

3. The method in accordance with claim 2 wherein said zinc-containing material is present in an amount of from about 0.5% to about 6% by weight, and wherein said chlorhexidine acetate is present in an amount of from about 0.2% to about 5% by weight.

4. A method of treating skin of dairy cattle, said method comprising applying a non-toxic, germicide, fungicide and healing composition in powdered form topically to said skin, said composition comprising (a) finely divided, particulate chlorhexidine acetate, and (b) an inert, powdered carrier, with said chlorhexidine acetate being present in an amount to achieve effective germicidal activity.

5. The method in accordance with claim 4 wherein said chlorhexidine acetate is present in an amount of from about 0.1% to about 12% by weight.

6. The method in accordance with claim 5 wherein said chlorhexidine acetate is present in an amount of from about 0.2% to about 5% by weight.

* * * * *

(12) INTER PARTES REEXAMINATION CERTIFICATE (0235th)
United States Patent
Petersson

(10) Number: US 7,208,170 C1
(45) Certificate Issued: Feb. 22, 2011

(54) POWDER TEAT DIP GERMICIDE, FUNGICIDE AND SKIN CONDITIONER

(75) Inventor: Lennart G. Petersson, Douglas, MA (US)

(73) Assignee: IBA Inc., Millbury, MA (US)

Reexamination Request:
No. 95/001,016, Nov. 16, 2007

Reexamination Certificate for:
Patent No.: 7,208,170
Issued: Apr. 24, 2007
Appl. No.: 10/660,880
Filed: Sep. 10, 2003

Related U.S. Application Data

(60) Provisional application No. 60/412,259, filed on Sep. 20, 2002.

(51) Int. Cl.
*A01N 25/32* (2006.01)

(52) U.S. Cl. ............... 424/406; 424/405; 424/409; 424/421; 424/438; 424/641; 424/642; 514/635

(58) Field of Classification Search ............... None
See application file for complete search history.

(56) References Cited

U.S. PATENT DOCUMENTS

| | | |
|---|---|---|
| 3,950,554 A | 4/1976 | Prince |
| 4,668,692 A | 5/1987 | Noorlander et al. |
| 5,211,961 A | 5/1993 | Adkinson |
| 5,370,875 A | 12/1994 | Rogozinski |
| 5,399,353 A | 3/1995 | Bartnik et al. |
| 5,641,498 A | 6/1997 | Loosemore |
| 5,942,239 A | 8/1999 | Huprich et al. |
| 6,183,785 B1 | 2/2001 | Westfall |

*Primary Examiner*—Evelyn Huang

(57) ABSTRACT

A non-toxic, germicide, fungicide and healing composition and a method of topically applying the composition in powdered form to the skin of domesticated farm animals including dairy cattle are disclosed. The composition comprises (a) finely divided, particulate chlorhexidine-containing material, (b) finely divided, particulate zinc-containing material and (c) an inert powdered carrier, with the chlorhexidine-containing material and the zinc-containing material being present in an amount to achieve effective germicidal activity. The chlorhexidine-containing material is preferably chlorhexidine acetate. The zinc-containing material is preferably selected from the group consisting of zinc stearate, zinc chloride, zinc nitrate, zinc oleate, zinc oxide, zinc phosphate, zinc peroxide, zinc iodide, elemental zinc and mixtures thereof.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-6 are cancelled.

\* \* \* \* \*